United States Patent [19]

Polski

[11] Patent Number: 5,019,072
[45] Date of Patent: May 28, 1991

[54] DISPOSABLE DIAPER THAT IS FASTENED BY CONTACT BETWEEN OVERLAPPING ADHESIVE PATCHES

[75] Inventor: Stephen P. Polski, Shoreview, Minn.

[73] Assignee: Minnesota Mining and Manufacturing Company, St. Paul, Minn.

[21] Appl. No.: 485,589

[22] Filed: Feb. 27, 1990

[51] Int. Cl.⁵ .................. A61F 13/15; C08L 9/00; C08L 51/00; C08L 23/00
[52] U.S. Cl. .................... 604/389; 604/390; 604/385.1; 525/98; 524/534; 524/536
[58] Field of Search .......... 428/355; 525/98; 524/534, 536; 604/385.1, 389, 366, 390

[56]  References Cited
U.S. PATENT DOCUMENTS

| 2,649,856 | 8/1953 | Le Bolt | 128/284 |
| 2,649,858 | 8/1953 | Le Bolt | 604/389 X |
| 2,704,732 | 3/1955 | Copeman et al. | 117/155 |
| 2,714,562 | 8/1955 | Hechtman | 117/68.5 |
| 2,962,404 | 11/1960 | McIntyre et al. | 154/46 |
| 3,049,228 | 8/1962 | Burnett | 206/58 |
| 3,089,494 | 5/1963 | Schwartz | 604/389 |
| 3,239,478 | 3/1966 | Harlan, Jr. | 260/27 |
| 3,635,861 | 1/1972 | Russell | 260/27 |
| 3,638,651 | 2/1972 | Torr | 128/284 |
| 3,917,607 | 11/1975 | Crossland et al. | 260/28.5 B |
| 3,932,328 | 1/1976 | Korpman | 525/98 X |
| 3,954,692 | 5/1976 | Downey | 260/33.6 AQ |
| 4,001,072 | 1/1977 | deNeui | 604/389 X |
| 4,136,071 | 1/1979 | Korpman | 524/534 |
| 4,163,077 | 7/1979 | Antonsen et al. | 604/390 X |
| 4,181,635 | 1/1980 | Takamatsu et al. | 525/98 X |
| 4,189,547 | 2/1980 | Osborn et al. | 525/99 |
| 4,288,567 | 9/1981 | Feeney et al. | 525/98 X |
| 4,399,249 | 8/1983 | Bildusas | 524/271 |
| 4,418,123 | 11/1983 | Bunnelle et al. | 525/98 X |
| 4,514,554 | 4/1985 | Hughes, et al. | 526/339 |
| 4,522,874 | 6/1985 | Pommez | 604/390 X |
| 4,526,577 | 7/1985 | Schmidt, Jr. et al. | 604/366 |
| 4,684,685 | 8/1987 | Schuman et al. | 524/270 |
| 4,699,622 | 10/1987 | Toussant et al. | 604/389 |
| 4,714,749 | 12/1987 | Hughes et al. | 525/98 X |
| 4,717,749 | 1/1988 | Tang et al. | 525/98 X |
| 4,728,572 | 3/1988 | Davis | 428/355 |
| 4,761,341 | 8/1988 | Rosiak et al. | 428/512 |
| 4,780,367 | 10/1988 | Lau et al. | 428/355 |

FOREIGN PATENT DOCUMENTS

| 189485 | 8/1988 | Japan . |
| 118604 | 5/1989 | Japan . |
| 138280 | 5/1989 | Japan . |
| 2116253B | 9/1965 | United Kingdom . |
| 2035053 | 6/1980 | United Kingdom | 604/390 |

Primary Examiner—Alan Cannon
Assistant Examiner—Elizabeth M. Burke
Attorney, Agent, or Firm—Gary L. Griswold; Roger R. Tamte; William J. Bond

[57]  ABSTRACT

A disposable diaper can be fastened securely around a person and be refastenable when it has an adhesive patch on the faces of corners at the back of the diaper, each of which patches contacts an adhesive patch on the front of the diaper, which patches form bonds to each other that have strong resistance to shear forces, can easily be peeled apart after 2 hours at room temperature and do not adhere either to ordinary packaging materials or to nonadhesive surfaces of the diaper. All of the adhesive patches can be cut from a single adhesive tape that has a flexible backing, one face of which bears a layer of the peelable adhesive while the other layer bears a layer of an adhesive that forms a strong, permanent bond to the diaper.

16 Claims, 1 Drawing Sheet

DISPOSABLE DIAPER THAT IS FASTENED BY CONTACT BETWEEN OVERLAPPING ADHESIVE PATCHES

CROSS-REFERENCE TO RELATED APPLICATION

A preferred adhesive for use in this invention is disclosed and claimed in an application entitled "Repositionable Adhesive Tape" (483,130(2-22-90)) filed of even date herewith. The disclosure in that application is incorporated herein by reference.

BACKGROUND AND FIELD OF THE INVENTION

The invention is concerned with disposable diapers that have refastenable adhesive closures and is specifically concerned with disposable diapers that are fastened by a two point closure system.

U.S. Pat. No. 4,699,622 (Toussant et al.) observes: "In general, disposable diapers all have the same basic structure which comprises an absorbent core encased between a liquid permeable user contacting topsheet and a liquid impermeable backsheet" (col. 1, lines 21-24). The diaper illustrated in the Toussant et al patent has an outer fastening means 54 bearing a pressure-sensitive adhesive layer that is adhered to the front of the diaper to encircle the wearer's waist. Almost every disposable diaper now on the market has such an outer fastening means consisting of two pressure-sensitive adhesive tapes at each ear of the back of the diaper as shown in FIGS. 1 and 3 of U.S. Pat. No. 3,848,594 (Buell). One of these tapes is a pressure-sensitive adhesive fastening tab which is initially protected by being folded over onto another tape, a release tape, from which it is peeled off by a "grip tab 48" to be in a position to adhere to the front of the diaper.

Although not shown in either the Toussant et al or the Buell patent, many disposable diapers have a third adhesive tape, namely a frontal tape which is contacted by the fastening tape.

The Toussant et al patent concerns the problem that disposable diapers tend to loosen due to the combined effects of forces generated by elasticized leg opening and movements of the diaper wearer. Its answer to this problem is to employ in addition to a conventional outer fastening means (54), as discussed above, an inner fastening means (60), such as a layer of adhesive applied to panels 62 that are "portions of the second waist portion 44 (the front of the diaper) which are overlain by the first waist portion 42 (the back of the diaper) when the diaper is fastened about the waist of the wearer" (col. 8, lines 48-51).

SUMMARY OF THE INVENTION

The invention provides a refastenable disposable diaper that is an improved means for avoiding the loosening problem of the Toussant et al patent, doing so in a more simple and economical way. The disposable diaper of the invention, like those of the Toussant et al. and Buell patents, can be a basic three-layer composite including a liquid-impervious outer shell or backsheet, and the back end of the diaper has a pair of ears that overlap corresponding opposite ears on the front end of the diaper when the diaper is wrapped around a person. By "ears" is meant the corners of the diaper, whether or not the diaper is I-shaped or rectangular.

The novel diaper differs from that of the Toussant patent by having:

preferably small patches of adhesive on the portions of the ears on opposite sides of the diaper that overlap when the diaper is worn specifically on the faces of these portions that will be in contact with each other when overlapped, which patches will form bonds to each other that have resistance to shear forces, can easily be peeled apart by hand after 2 hours at room temperature and preferably at 37° C., and preferably do not adhere either to ordinary packaging materials or to nonadhesive surfaces of the diaper so that the adhesive patches do not need to be protected during handling and shipment.

The peelable adhesive patch should not adhere either to ordinary packaging materials or to nonadhesive surfaces of the diaper when its "T-Peel Value" (as herein defined) does not exceed 2N/25 mm of width, and may not adhere even at a T-Peel Value as high as 7N/25 mm.

THE DRAWINGS

The invention may be more easily understood in reference to the drawings, in which:

FIG. 1 is a schematic isometric view of a disposable diaper of the invention; and FIG. 2 is a schematic isometric view of a disposable diaper similar to that of FIG. 1 as it would appear while being worn by a person.

DETAILED DESCRIPTION OF PREFERRED EMBODIMENTS

Figure 1:
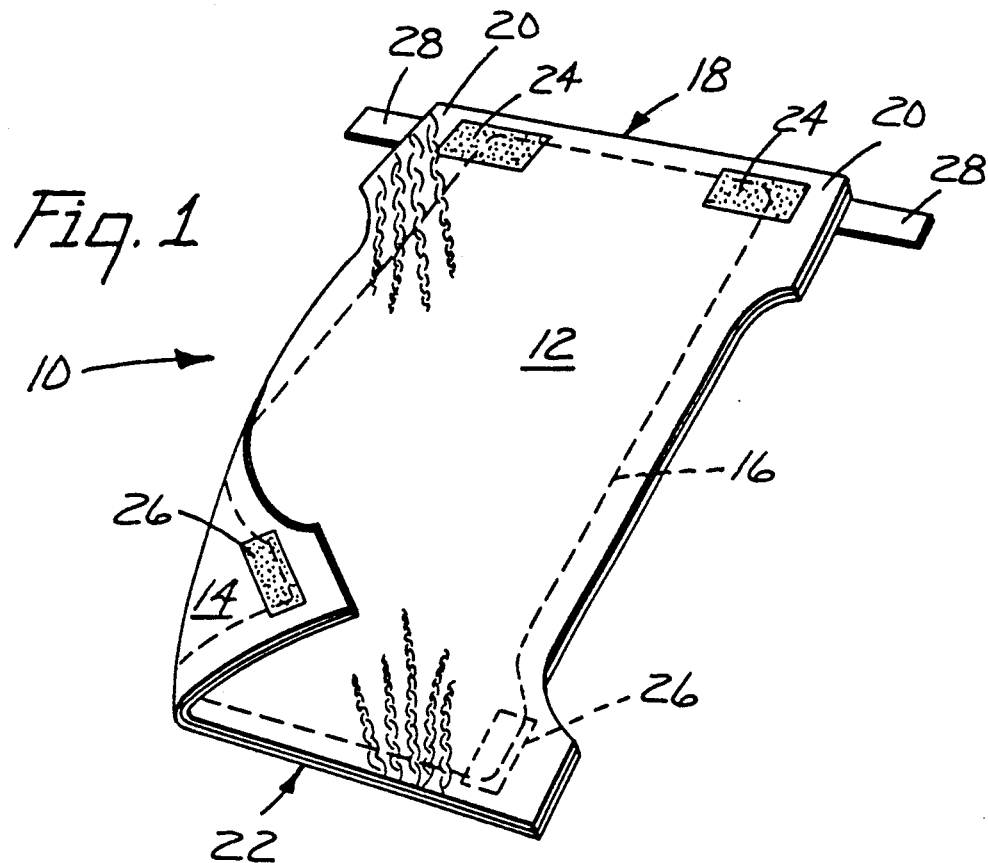

The disposable diaper 10 shown in FIG. 1 is a three-layer composite including a liquid-permeable user-contacting topsheet 12 (topsheet face), a liquid-impervious outer shell (backsheet) 14, and absorbent layer 16. At the back 18 of the diaper are a pair of ears 20 that overlap the front 22 of the diaper when the diaper is being worn. On the topsheet side of each of the ears 20 is a patch 24 of peelable adhesive, and on the outer shell 14 at the front 22 of the diaper are two patches 26 of peelable adhesive. When the diaper 10 is wrapped around a person to assume the shape of the diaper 30 shown in FIG. 2, each of the patches 24 at the ears 20 contacts one of the patches 26 at the front 22 of the diaper. Projecting from each of the ears 20 is a pressure-sensitive adhesive fastening tab 28 constituting an a outer fastening means.

The fastening tab adhesive is generally tacky and must be protected during nonuse. Generally this can be done with a detachable release tape (not shown) or by zone coating the tab with adhesive and release coatings so that the adhesive portion can fold over onto the release coated portion (not shown). It may also be possible to use a release tape (not shown) on the topsheet if the adhesive patches are suitably located above or below the release tape.

By "a small patch of adhesive" is meant that the peelable adhesive at each of the ears of the diaper covers an area generally not exceeding 50 cm$^2$. However, this is a commercially practical limit only, and if desired, larger patches can be used. However, larger patches would be wasteful of material.

Conventionally, the outer fastening means of Toussant et al is a fastening tab located at the back ears of the diaper, which ears will overlap the front ears permitting the tab to be attached to the front portion of the outer shell. In this case, the peelable adhesive patches will be placed on the back ears on the topsheet face and on the front ears on the outer shell. Preferably, when the disposable diaper is of a size to be worn by an infant, each patch of adhesive at the back ears of the diaper is from 3 to 6 cm in length and from 1.5 to 3 cm in width, with the lengthwise direction parallel to the lengthwise direction of the waist band. When the patches of peelable adhesive at the front ears of the diaper are of economically small size, a back adhesive patch length less than 3 cm might not allow enough leeway for wearers of different size, while a length of more than 6 cm might be economically wasteful.

Although the peelable adhesive at the front of the diaper can be a continuous strip across the front of the diaper, for great leeway in sizes of wearers, there preferably is a separate patch of peelable adhesive at each side or ears at the front of the diaper, and each patch is from 3 to 6 cm in length and from 1.5 to 3 cm in width, with the lengthwise direction extending orthogonally to the waist band lengthwise direction. When the adhesive patches are within these preferred sizes, the diaper can be wrapped snugly around an infant's waist and legs while ensuring a high likelihood of adhesive-to-adhesive contact across the full width of each peelable adhesive patch. This might not always be accomplished if the front adhesive patches were less than 3 cm in length.

If the widths of both the front and back peelable adhesive patches are less than 1.5 cm, there could be a hazard of inadequate holding power, while widths of greater than 3 cm would be wasteful of material. The preferred range of overlap in a diaper of the invention of the peelable adhesive patches will also generally give values which greatly exceed the shear resistance values specified as needed by Toussant et al; namely, a shear resistance of greater than 500 gms, even when the patches are at their minimum width of 1.5 cm, for an overlap of 2.25 cm. Consequently, with peelable adhesives that will agressively bond, it is possible to use patch widths of less than 1.5 cm and still achieve acceptable shear resistance values.

When the back peelable adhesive patches have the preferred widths, or the more preferred width of 2.5 cm, the force to peel the adhesive patches apart is easily controlled to be within desirable ranges for an "inner fastening means" as per the Toussant et al patent, e.g., generally from 1 to 12N(Newtons), preferably between 4 and 7N.

The patches of peelable adhesive on the top sheet or inner face of each of the back ears and on the overlapped portions at the front ears can function as the "inner fastening means" of the Toussant et al patent. A great advantage of a diaper of the invention lies in its simplicity to manufacture, cost and the avoidance of the necessity of protective release tapes, as the adhesive is preferably tack-free or of low tack. With a tack-free adhesive there is no need for a protective tape while low tack adhesives are generally releaseable.

Figure 2:
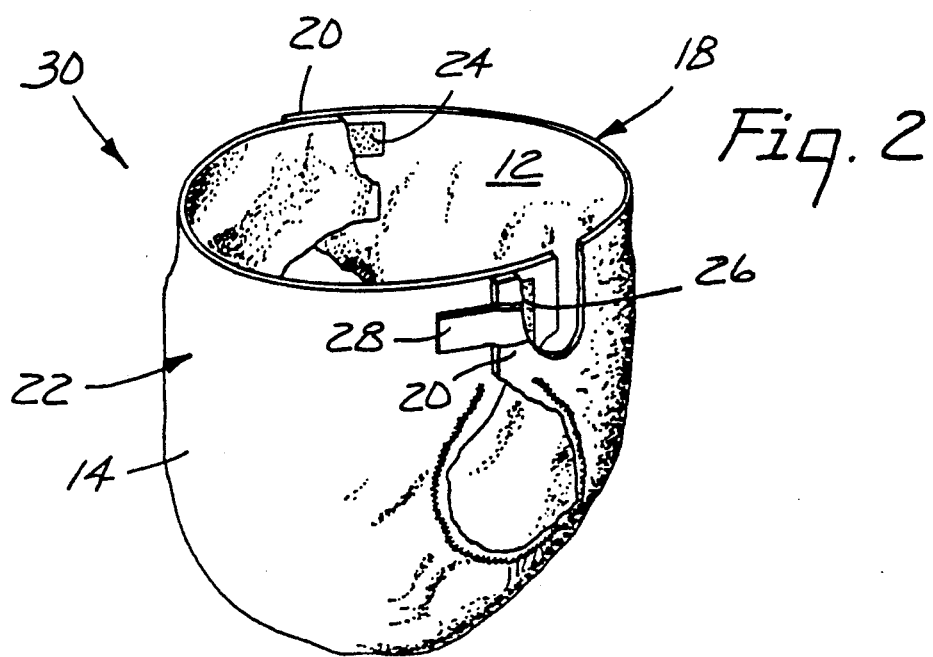

The FIG. 2 disposable diaper 30 is the same as that of FIG. 1 except that it is shown as it is worn. The peelable adhesive patch 24 will intersect with the peelable adhesive patch 26.

In the manufacture of the novel disposable diaper, the peelable adhesive patches can be one layer of a double-coated tape, that preferably has a flexible backing, and a non-peelable adhesive layer of which aggressively adheres to the diaper under moderate pressure. The peelable adhesive patches can also be applied as single-layer tapes, the backings of which are selected to permit them to become ultrasonically bonded to the diaper. For example, a polypropylene tape backing can be ultrasonically bonded to the topsheet of most disposable diapers, and a polyethylene tape backing can be ultrasonically bonded to the backsheet or outer shell, which typically is polyethylene. It also should be feasible to hot-melt coat the peelable adhesive patches directly onto each of the topsheet and outer shell, although it may be necessary first to apply a primer coating or other conventional treatments, such as corona, to enhance adhesion of the peelable adhesive to the topsheet or outer shell.

The peelable adhesive layer of each of the patches preferably is the peelable adhesive disclosed in the above-cited application Ser. No. 483,130 (2-22-90). Briefly, that peelable adhesive comprises a composition of by weight:

from 20 to 80 parts of at least one elastomeric block copolymer selected from styrene/butadiene (S-B-S), styrene/isoprene (S-I-S), and styrene/ethylene-butylene (S-EB-S) block copolymers, and correspondingly from 80 to 20 parts of tackifying material selected from tackifier resin and a blend of tackifier resin and liquid plasticizer oil, which peelable adhesive is hot-melt coatable and has a composite midblock glass transition temperature (CMTg) from 220 Kelvin to 240 Kelvin when the adhesive is based on styrene/isoprene or styrene/ethylene-butylene block copolymers and a CMTg from 215 Kelvin to 235 Kelvin when the adhesive is based on styrene/butadiene block copolymer. The calculated CMTg is determined using the Fox Equation (given below) and the measured glass transition temperature (Tg) of each of the components in the adhesive. The Tg for each component is measured using a differential scanning calorimeter such as a DSC-7, manufactured by Perkin-Elmer. The Tg is measured on the second heating run using a scan rate of 20 degrees Centigrade per minute. The first heating run is made up to well above the softening point of the test material. The sample is subsequently quenched to well below the Tg of the material. Antioxidants added to the adhesive are not figured into the calculation of the CMTg.

$$\frac{\Sigma W_i}{CMTg} = \Sigma \frac{W_i}{Tg_i} \qquad \text{Fox Equation}$$

where $W_i$ is the weight fraction of component i and $Tg_i$ is the glass transition temperaure of component i. Only the midblock portion of the block copolymer is included in the calculation of the CMTg. For a styrene/isoprene/styrene block copolymer, the midblock portion is the polyisoprene portion of the molecule.

These peelable adhesives show quite strong self bonding and generally can be used in patches even smaller than those preferred. Because that peelable adhesive is hot-melt coatable, it can be economically coated onto a flexible backing at very high speeds, thus providing a further economy. Furthermore, because it can be hot-melt coated without evolution of volatiles, its use is environmentally advantageous. Although these peelable adhesives are presently preferred, any suitable peelable adhesive known in the art would be useful for the peelable adhesive patches of the invention.

When the proportion of elastomeric block copolymer is near the high end (i.e., 55-80 parts) and the CMTg is near the high end (i.e within 10° Kelvin) of the aforementioned ranges, it has been found that these preferred peelable adhesives generally show characteristics that are best suited to diaper closure systems. Namely, these adhesives show a relatively high resistance to shear forces, are low-tack or tack-free and exhibit a low adhesive buildup to itself at body temperatures. Most preferably the CMTg is within 5 Kelvin of the high end of the aforementioned ranges.

Testing

Testing was carried out using tapes having a backing of biaxially oriented poly(ethylene terephthalate) film having a thickness of 12.5 μm. Two pieces of each tape to be tested, each 2.5 cm in width, were placed adhesive-to-adhesive and tested after being subjected to one pass in each direction of a 500 gm hard rubber roller at 12 inches (30 cm) per minute. Testing included:

180° Dynamic Shear Value

This value was determined using ASTM Test Method D3528-76 at a crosshead speed of 10 inches (25 cm) per minute.

Hand Shear Value

The ends of the two pieces were pulled 180° apart by hand and qualitatively judged as to whether they had adequate resistance to shear forces to keep a diaper securely fastened. When one of the tape backings broke, the Hand Shear Value was adjudged to be "good". In instances of bond failure without breaking of a backing, the Hand Shear Value was adjudged as "acceptable", when the force to failure was nearly as great as was required to break a backing. The Hand Shear Value was adjudged to be "poor" when the bond failed under a force that would probably be too low for diaper use.

T-Peel Value

This value was determined using ASTM Test Method D1876-72 at a crosshead speed of 10 inches (25 cm) per minute.

Hand Peel Value

The ends of the two pieces were tested for T-peel by hand and qualitatively judged in comparison to closures of typical commercial disposable diapers. The Hand Peel Value was judged to be;

"good" about equalling commercial diaper fastening tapes,

"fair" at the minimum for commercial fastening tapes,

"poor" when deemed to be too low for commercial use, and

"none" when there was virtually no resistance to peel.

When the peel was adjudged too shocky for commercial use in a disposable diaper, it was reported as "shocky".

Materials used in the following examples include:

"Kraton" 1657 S-EB-S block copolymer from Shell Chemical Co.

"Kraton" 1107 S-I-S block copolymer

"Estane" 5730P polyurethane elastomer from B. F. Goodrich Co.

"Nepol" DN 1201L butadiene/acrylonitrile rubber from Nippon-Zeon

"Res" D-2084 fully hydrogenated solid hydrocarbon resin from Hercules, Inc.

"Regalrez" 1018 from Hercules, Inc.

"Wingtack Plus" solid C5 aliphatic resin from Goodyear Tire & Rubber Co.

"Zonarez" A-25 alpha-pinene liquid resin from Arizona Chemical Co.

In the examples, all parts are given by weight.

EXAMPLE 1

A handspread of 50% solution, in toluene, of 70 parts of "Kraton" 1657 and 30 parts of "Res" D-2084 was pulled onto biaxially oriented poly(ethylene terephthalate) film having a thickness of 12.5 μm. The dried coating weight was about 24 g/m$^2$. The adhesive of Example 1 had:

CMTg=238 Kelvin
180° Dynamic Shear Value=588 N/cm$^2$
T-Peel Value=6.5 N/25 mm

EXAMPLES 2-8

A series of adhesive compositions were prepared in the proportions indicated in Table I.

TABLE I

| Ex | Kraton 1657 | Kraton 1107 | Estane 5730P | Res D-2084 | Regalrez 1018 | Wingtack Plus | Zonarez A-25 |
|---|---|---|---|---|---|---|---|
| 2 | 70 | | | 30 | | | |
| 3 | 80 | | | 20 | | | |
| 4 | 70 | | | | 30 | | |
| 5 | 80 | | | | 20 | | |
| 6 | | 80 | | | | 20 | |
| 7 | | 80 | | | | | 20 |
| 8 | | | 100 | | | | |

Handspreads of each of the adhesive compositions of Examples 2-8 were prepared as in Example 1. Example 2 was a repeat of Example 1. The adhesive of each Example was tested as reported in Table II which also reports the thumb appeal under the column headed "Tack". "Some" tack indicates greater tack than "low" and less than "fair". In general, adhesives having either "none" or "low" thumb appeal do not adhere either to ordinary packaging materials or to nonadhesive surfaces of ordinary disposable diapers. In certain circumstances even adhesives with some tack can be used without a protective tape.

TABLE II

| Ex | CMTg (Kelvin) | Tack | Hand Shear Value | Hand Peel Value |
|---|---|---|---|---|
| 2 | 238 | None | Good | Good |
| 3 | 230 | None | Good | Fair |
| 4 | 225 | None | Adequate | Fair |
| 5 | 222 | None | Adequate | Fair |
| 6 | 231 | Some | Good | Fair |
| 7 | 222 | Some | Good | Fair |
| 8 | — | None | Good | None |

Additional test pairs of pieces of the adhesive of Examples 2 and 8 were subjected to body temperature (37° C.) for two hours. This caused the pieces of the adhesive of Example 8 to block so that they could not be peeled apart, but produced no noticeable change in those of Example 2.

EXAMPLES 9-11

Three adhesive compositions were prepared in the proportions indicated in Table III which also indicates testing.

TABLE III

| Ex | "Kraton" 1657 | "Res" D-2084 | CMTg (Kelvin) | Tack | Hand Shear Value | Hand Peel Value |
|---|---|---|---|---|---|---|
| 9  | 60 | 40 | 247 | Low  | Good | Good   |
| 10 | 50 | 5  | 255 | Some | Good | Fair   |
| 11 | 40 | 60 | 264 | Fair | Good | Shocky |

The hand peel of the adhesive of Example 10 was starting to become shocky and hence marginal in this respect.

The adhesives of Examples 6, 7, 10 and 11 were adjudged to be sufficiently tacky that it might be desirable to cover them, e.g., by a release liner, during shipment of a disposable diaper.

EXAMPLE 12

A urethane acrylate adhesive was spread onto a poly(vinyl chloride) substrate. The urethane acrylate was that described in Example 1 of U.S. patent application Ser. No. 07/427,448 to Shih-Lai Lu et al applied to a thickness of 0.125 mm on a 0.051 mm substrate. The acrylate was cured with ultraviolet lamps at 4 mW/cm$^2$, for a total exposure of 900 mJ.

The adhesive of Example 12 had no tack either to the thumb or to polyethylene. Both its Hand Shear Value and its Hand Peel Value were good.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A refastenable disposable diaper comprising a composite including an absorbent core encased between a liquid-permeable user-contacting topsheet and an outer shell of thin thermoplastic film, the back of the composite having a pair of ears that overlap ears on the front of the diaper when the diaper is wrapped around a person, wherein said diaper has outer fastening means for holding the diaper in its wrapped position, further comprising an inner fastening means comprising peelable adhesive patches on faces of the back and front ears of the diaper that overlap when the diaper is in its wrapped position, and which places the patches in contact with each other, which patches will form bonds to each other that have resistance to shear forces and can be peeled apart by hand after 2 hours at room temperature.

2. A disposable diaper as defined in claim 1 and having a separate patch of said peelable adhesive at each ear at the front of the diaper.

3. A disposable diaper as defined in claim 2 having a separate patch of said peelable adhesive at each ear at the back of the diaper wherein each patch of said peelable adhesive at the back of the diaper is from 3 to 6 cm in length and from 1.5 to 3 cm in width, with the lengthwise direction parallel to the waist band lengthwise direction.

4. A disposable diaper as defined in claim 3 wherein each patch of said peelable adhesive at the front of the diaper is from 3 to 6 cm in length and from 1.5 to 3 cm in width, with the lengthwise direction orthogonal to the waist band lengthwise direction.

5. A disposable diaper as defined in claim 1 wherein each of said patches of peelable adhesive is cut from a single adhesive tape that has a flexible backing, one face of which bears a layer of peelable adhesive while the other layer bears a layer of an adhesive that will permanently bond to the topsheet or the outer shell of the diaper.

6. A disposable diaper as defined in claim 1 wherein when two of said peelable adhesive patches are bonded to each other, the force to peel them apart is from 1 to 12N.

7. A disposable diaper as defined in claim 1 wherein each of said peelable adhesive patches has a T-Peel Value (as herein defined) not exceeding 7N/25 mm.

8. A disposable diaper as defined in claim 7 wherein each of said adhesive patches has a T-Peel Value not exceeding 2N/25 mm.

9. A disposable diaper as defined in claim 1 wherein a patch of said peelable adhesive is carried by a flexible backing that is ultrasonically bonded to one of the topsheets and the outer shell.

10. A disposable diaper as defined in claim 9 wherein said flexible backing is a polyethylene film.

11. A disposable diaper as defined in claim 9 wherein said flexible backing is a polypropylene film.

12. A disposable diaper as defined in claim 1 wherein said outer fastening means comprises at least a pair of pressure-sensitive adhesive fastening tabs.

13. A disposable diaper as defined in claim 1 wherein the peelable adhesive of each of the patches comprises a composition of by weight:
   from 20 to 80 parts of at least one elastomeric block copolymer selected from styrene/butadiene, styrene/isoprene, and styrene/ethylene-butylene block copolymers, and
   correspondingly from 80 to 20 parts of tackifying material selected from tackifier resin and a blend of tackifier resin and liquid plasticizer oil,
which peelable adhesive is hot-melt coatable and has a composite midblock glass transition temperature (CMTg) from 220 Kelvin to 240 Kelvin when the adhesive is based on styrene/isoprene or styrene/ethylene-butylene block copolymers and a CMTg from 215 Kelvin and 235 Kelvin when the adhesive is based on styrene/butadiene block copolymer.

14. A disposable diaper as defined in claim 13 wherein the elastomeric block copolymer comprises from 55 to 80 parts by weight of the peelable adhesive composition.

15. A disposable diaper as defined in claim 13 wherein the CMTg of the peelable adhesive is within 10 Kelvin of the top of an aforementioned range.

16. A disposable diaper as defined in claim 1 wherein said peelable adhesive is a low or no tack adhesive which adhesive does not adhere to ordinary packaging materials or to nonadhesive surfaces of the diaper so as not requiring a protective release tape.

* * * * *